US009161760B2

(12) United States Patent
Suarez et al.

(10) Patent No.: US 9,161,760 B2
(45) Date of Patent: Oct. 20, 2015

(54) SURGICAL TOOL FOR ROBOTIC ARM WITH ROTATING HANDLE

(75) Inventors: Joseph Suarez, Plantation, FL (US); Brian Schmitz, Fort Lauderdale, FL (US)

(73) Assignee: Mako Surgical Corporation, Fort Lauderdale, FL (US)

( * ) Notice: Subject to any disclaimer, the term of this patent is extended or adjusted under 35 U.S.C. 154(b) by 867 days.

(21) Appl. No.: 13/339,608

(22) Filed: Dec. 29, 2011

(65) Prior Publication Data

US 2013/0172903 A1    Jul. 4, 2013

(51) Int. Cl.
*A61B 17/14*    (2006.01)
*A61B 17/16*    (2006.01)
*A61B 19/00*    (2006.01)
*A61B 17/00*    (2006.01)

(52) U.S. Cl.
CPC ............. *A61B 17/14* (2013.01); *A61B 17/1622* (2013.01); *A61B 19/2203* (2013.01); *A61B 19/50* (2013.01); *A61B 19/5244* (2013.01); *A61B 2017/0042* (2013.01); *A61B 2019/2292* (2013.01)

(58) Field of Classification Search
CPC ................... A61B 19/2203; A61B 2017/042; A61B 17/14; A61B 19/50
See application file for complete search history.

(56) References Cited

U.S. PATENT DOCUMENTS

| 9,060,794 B2 * | 6/2015 | Kang et al. ............................ 1/1 |
| 2009/0012532 A1 * | 1/2009 | Quaid et al. ................... 606/130 |
| 2011/0082462 A1 | 4/2011 | Suarez et al. |
| 2015/0164600 A1 * | 6/2015 | Hagag et al. ..................... 606/79 |

* cited by examiner

*Primary Examiner* — Andrew Yang
(74) *Attorney, Agent, or Firm* — Miller, Matthias & Hull LLP

(57) ABSTRACT

A surgical tool is disclosed that may be rotatably mounted to a surgical robotic arm. The surgical tool is rotatable about a first axis that is at least substantially vertical when the robotic arm is in a horizontal position. The surgical tool includes a housing that is coupled to the arm and rotatable about the first axis. The housing is at least substantially cylindrical and defines a second axis that is at least substantially perpendicular to the first axis. The tool also includes a handle that includes a grip that is coupled to a sleeve. The sleeve rotatably accommodates at least part of the housing. As a result, the handle and sleeve may be rotated about the second axis while the housing remains fixed with respect to the second axis.

30 Claims, 6 Drawing Sheets

US 9,161,760 B2

SURGICAL TOOL FOR ROBOTIC ARM WITH ROTATING HANDLE

TECHNICAL FIELD

This disclosure relates generally to robotic surgical systems and, more particularly, to cutting tools for robotic surgical systems for orthopedic joint replacement surgeries. More specifically, this disclosure relates to a surgical tool mounted at the end of a robotic arm with an ergonomic grip that can be adjusted without changing the orientation or pose of the surgical tool.

BACKGROUND

Robotic systems are often used in applications that require a high degree of accuracy and/or precision, such as surgical procedures. Robotic systems may include various types of robots, such as autonomous, tele-operated, and interactive. Interactive robotic systems are preferred for some types of surgery, such as joint replacement surgery, because they enable a surgeon to maintain direct, hands-on control of the surgical procedure while still achieving a high degree of accuracy and/or precision.

For example, in joint replacement surgery, a surgeon may use an interactive, haptically guided robotic arm in a passive manner to sculpt or cut bone to receive a joint implant. To cut bone, the surgeon manually grasps and manipulates the robotic arm to move a surgical tool that includes a cutting implement (e.g., surgical saw, burr, reamer etc.) that is coupled to the end of the robotic arm to cut the bone. As long as the surgeon maintains a cutting implement within a predefined virtual cutting boundary, the robotic arm moves freely with low friction and low inertia such that the surgeon perceives the robotic arm as essentially weightless and can move the robotic arm as desired. If the surgeon attempts to move the cutting implement outside the virtual cutting boundary, however, the robotic arm provides haptic (or force) feedback that prevents or inhibits the surgeon from moving the cutting implement beyond the virtual cutting boundary. In this manner, use of a robotic arm provides highly accurate, repeatable bone cuts. When the surgeon manually installs the implant on a corresponding bone cut, the implant will generally be accurately aligned due to the configuration of and interface between the cut bone and the implant.

For ergonomic reasons, a surgical tool mounted on an end of a robotic arm will typically include a handle or a grip in addition to a surgical implement such as a saw, reamer or burr. Some surgical procedures require maintaining an appropriate cutting boundary in addition an accurate angular orientation or pose of surgical implement. However, positioning the surgical implement within the correct cutting boundary and at the correct angular orientation often causes the grip, which is fixed with respect to the surgical implement, to assume an ergonomically uncomfortable position for the surgeon.

Therefore, there is a need for improved surgical tools that can be mounted on interactive robotic arms that include grips that can be adjusted positionally without affecting the position and accurate location of the surgical cutting implement (e.g., surgical saw, burr, reamer etc.) that has been placed within the correct cutting boundary and at the correct angular orientation or pose.

SUMMARY OF THE DISCLOSURE

In an embodiment, a surgical tool is disclosed that is rotatably mounted to a robotic arm. The tool is rotatable about a first axis that is at least substantially vertical when the robotic arm is in a horizontal position. The surgical tool includes a housing coupled to the robotic arm and rotatable about the first axis. The housing is at least substantially cylindrical and defines a second axis that is at least substantially perpendicular to the first axis. The housing includes a plurality of recesses circumferentially spaced apart around the housing and about the second axis. The surgical tool also includes a handle that includes a grip that is coupled to a sleeve. The sleeve rotatably accommodates at least part of the housing and at least partially covers the recesses. The sleeve is coupled to a lock assembly that includes a lock rod sized to be at least partially received and one of the recesses at a time. When the lock rod is moved radially outwardly beyond the recesses, the handle and sleeve may be rotated about the second axis while the housing remains fixed with respect to the second axis. As a result, the position of the handle may be adjusted without effecting the pose, position or angular orientation of the surgical tool.

A surgical robotic system is also disclosed. The surgical robotic system includes a robotic arm and a surgical tool rotatably mounted to the robotic arm. The surgical tool is rotatable about a first axis that is at least substantially vertical when the robotic arm is in a horizontal position. The tool includes a housing that is coupled to the robotic arm. The housing is at least substantially cylindrical and defines a second axis that is at least substantially perpendicular to the first axis. The housing is coupled to a surgical implement such as a saw, reamer, burr, etc. The housing includes a plurality of recesses circumferentially spaced apart around the housing and about the second axis. The recesses are also aligned in a plane that is at least substantially perpendicular to the second axis. The housing is rotatable with the surgical tool about the first axis but the housing is not rotatable about the second axis. The surgical tool also includes a handle that includes a grip coupled to a sleeve. The sleeve rotatably accommodates at least part of the housing and at least partially covers the recesses in the housing. The sleeve is coupled to a lock assembly that includes a button that includes a lock rod sized to be at least partially received in one of the recesses at a time. The button and lock rod are biased so the lock rod is biased radially inwardly towards the recesses in the housing. When the button is pressed, thereby overcoming the radially inward bias and thereby lifting the lock rod radially outward beyond the recesses, the handle may be rotated about the second axis while the housing and surgical implement remain fixed with respect to the second axis.

A method is disclosed for rotating a grip of a surgical tool while maintaining a surgical implement coupled to the surgical tool in a fixed position or pose. The method includes rotatably mounting the surgical tool to a robotic arm. The surgical tool is rotatable about a first axis that is at least substantially vertical when the robotic arm is in a horizontal position. The surgical tool includes a housing coupled to the robotic arm and that is rotatable about the first axis. The housing is at least substantially cylindrical and defines a second axis that is at least substantially perpendicular to the first axis. The housing includes a plurality of recesses circumferentially spaced apart around the housing and about the second axis. The surgical tool also includes a handle that includes a grip coupled to a sleeve. The sleeve rotatably accommodates at least part of the housing and at least partially covers the recesses in the housing. The sleeve is coupled to a lock assembly that includes a lock rod sized to be at least partially received in one of the recesses at a time. The method also includes moving the lock rod radially outwardly away from a first recess. The method further includes rotating the handle about the second axis while the housing remains fixed with respect to the second axis. The method further includes aligning the lock rod with a second recess and moving the lock rod radially inwardly towards the second recess so that it is at least partially received in the second recess.

In any one or more of the embodiments described above, the lock assembly further includes a button that engages the lock rod. The button and lock rod are biased so the lock rod is biased radially inwardly towards the recesses in the housing. When the button is pressed, the pressing action overcomes the radially inward bias of the lock rod and the lock rod may be lifted radially outwardly beyond the recesses. In this position, the handle may be rotated about the second axis without affecting the position of the housing or surgical implement coupled to the housing.

In any one or more of the embodiments described above, the button includes a first end and a second end with a pivot pin disposed therebetween. The pivot pin may be coupled to the sleeve. The first end of the button may be biased outwardly by a spring causing the second end of the button to be biased inwardly towards the lock rod to move the lock rod towards the recesses.

In any one or more of the embodiments described above, the lock rod may be slidably coupled to the button by a pin.

In any one or more of the embodiments described above, the housing may include from two to about ten recesses.

In any one or more of the embodiments described above, the handle may be rotatable about 180° around the housing and about the second axis.

In any one or more of the embodiments described above, the housing may include a first end coupled to a surgical implement. The housing may also include a second end that includes the recesses. The robotic arm may be coupled to the housing between the first and second ends of the housing.

In any one or more of the embodiments described above, the housing may be coupled to a surgical implement selected from the group consisting of a blade, a reamer and a burr.

In any one or more of the embodiments described above, the handle includes a loop that accommodates a first end of the housing while the sleeve accommodates a second end of the housing with the robotic arm being coupled to the housing between the loop and the sleeve.

In any one or more of the embodiments described above, the handle may further include a trigger. The trigger may be coupled to a link. The link may abuttingly engage a magnet. The housing may enclose a printed circuit board (PCB) that includes a plurality of Hall effect sensors. The PCB may be disposed between the robotic arm and the recesses in the housing. Upon engagement by the link, the magnet is slidable along the Hall effect sensors with the housing disposed between the magnet and the Hall effect sensors.

In any one or more of the embodiments described above, the housing may enclose a first end and a second end with the arm being coupled to the housing between the first and second ends. The first end of the housing may be coupled to a surgical implement. The magnet may be coupled to a ring. The second end of the housing accommodates the ring and the sleeve with the ring disposed between the sleeve and the housing. The second end of the housing also encloses the PCB. Upon engagement by the link, the magnet and ring are slidable across the Hall effect sensors with the housing disposed between the magnet/ring and the Hall effect sensors.

In any one or more of the embodiments described above, the recesses disposed in the housing are aligned in a plane that may be at least substantially perpendicular to the second axis.

In any one or more of the embodiments described above, the housing may also include a motor coupled to a surgical implement. The handle may also include a trigger, which may be coupled to a link. The link may be coupled to a magnet. The housing may enclose a PCB and a plurality of Hall effect sensors. The method may further include adjusting a speed of the motor by moving the magnet with the link by pressing or releasing the trigger thereby sliding the magnet across the Hall effect sensors with the housing disposed between the magnet and the Hall effect sensors.

DETAILED DESCRIPTION

Figure 1:
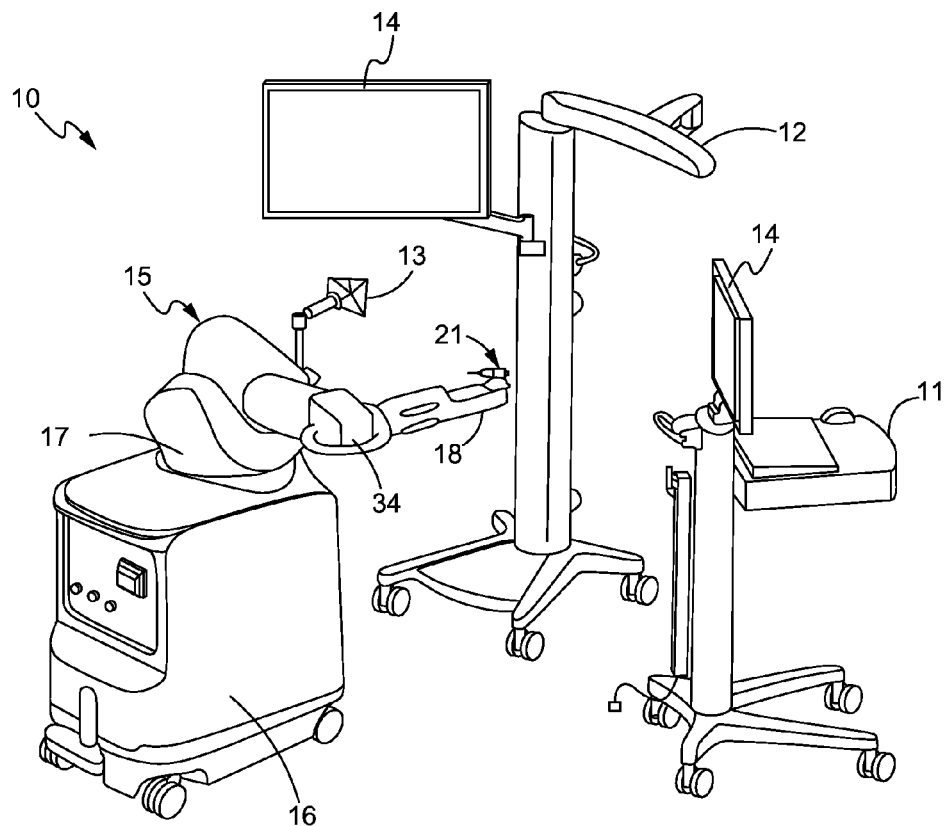
FIG. 1 is a perspective view of a robotic surgical system.
Figure 2:
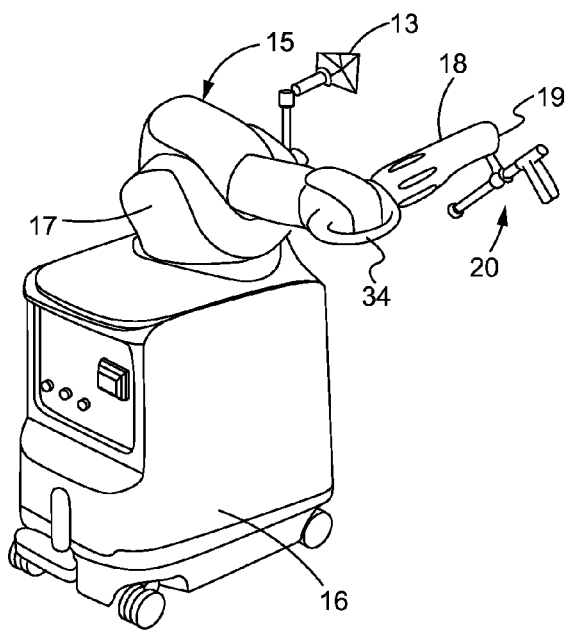
FIG. 2 is a perspective view of a surgical robotic arm used with the system of FIG. 1.

Referring to FIG. 1, a surgical robotic system 10 is shown which can be used for various procedures, including, but not limited to, joint replacements, such as hip replacements. As shown in FIG. 1, the surgical system 10 includes a computer assisted navigation system 11, tracking devices 12, 13, one or more displays 14, a robotic arm 15 pivotally mounted to a base 16, which includes various control components and a controller. As shown in FIG. 2, the robotic arm 15 includes a base portion 17 and an articulated arm 18. The arm 18 includes a distal end 19 which is pivotally coupled to a surgical tool shown generally at 20 in FIG. 2 while a different tool 21 is shown in FIG. 1.

The force system and controller are configured to provide control or guidance to the surgeon during manipulation of the surgical tool. The force system is configured to provide at least some force to the surgical tool via the articulated arm 18, and the controller (not shown; typically housed in the base 16) is programmed to generate control signals for controlling the force system. In one embodiment, the force system includes actuators and a back-driveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. Patent Application Publication No. 2010/0106511, each of which is hereby incorporated by reference herein in its entirety. In one embodiment, the surgical system is the RIO™ Robotic Arm Interactive Orthopedic System manufactured by MAKO Surgical Corp. of Fort Lauderdale, Fla., USA.

The tracking devices 12, 13 are configured to track the relative locations of the surgical tool 20, 21 that is coupled to the articulated arm 18 and the patient's anatomy. The surgical tool 20, 21 can be tracked directly by the tracking devices 12, 13. Alternatively, the pose of the surgical tool 20, 21 can be determined by tracking the location of the base 16 and calculating the pose of the surgical tool 20, 21 based on joint encoder data from joints of the robotic arm 15 and a known geometric relationship between the surgical tool 20, 21 and the robotic arm 15. In particular, the tracking devices 12, 13 (e.g., an optical, mechanical, electromagnetic, or other known tracking system) tracks (or enables determination of) the pose (i.e., position and orientation) of the surgical tool 20, 21 and the patient's anatomy so the navigation system 11 knows the relative relationship between the tool 20, 21 and the patient's anatomy (not shown).

In operation, a user (e.g., a surgeon) manually moves the robotic arm 15 to manipulate the surgical tool 20, 21 to perform a surgical task on the patient, such as bone cutting or implant installation. As the surgeon manipulates the tool 20, 21, the tracking devices 12, 13 track the location of the surgical tool 20, 21 and the robotic arm 15 and provides haptic (or force) feedback to limit the surgeon's ability to move the tool 20, 21 beyond a predefined virtual boundary that is registered (or mapped) to the patient's anatomy, which results in highly accurate and repeatable bone cuts and/or implant placement. The robotic arm 15 operates in a passive manner and provides haptic feedback when the surgeon attempts to move the surgical tool beyond the virtual boundary. The haptic feedback is generated by one or more actuators (e.g., motors) in the robotic arm 15 and transmitted to the surgeon via a flexible transmission, such as a cable drive transmission. When the robotic arm 15 is not providing haptic feedback, the robotic arm 15 is freely moveable by the surgeon and preferably includes a virtual brake that can be activated as desired by the surgeon. During the surgical procedure, the navigation system 11 displays images related to the surgical procedure on one or both of the displays 14.

Figure 3:
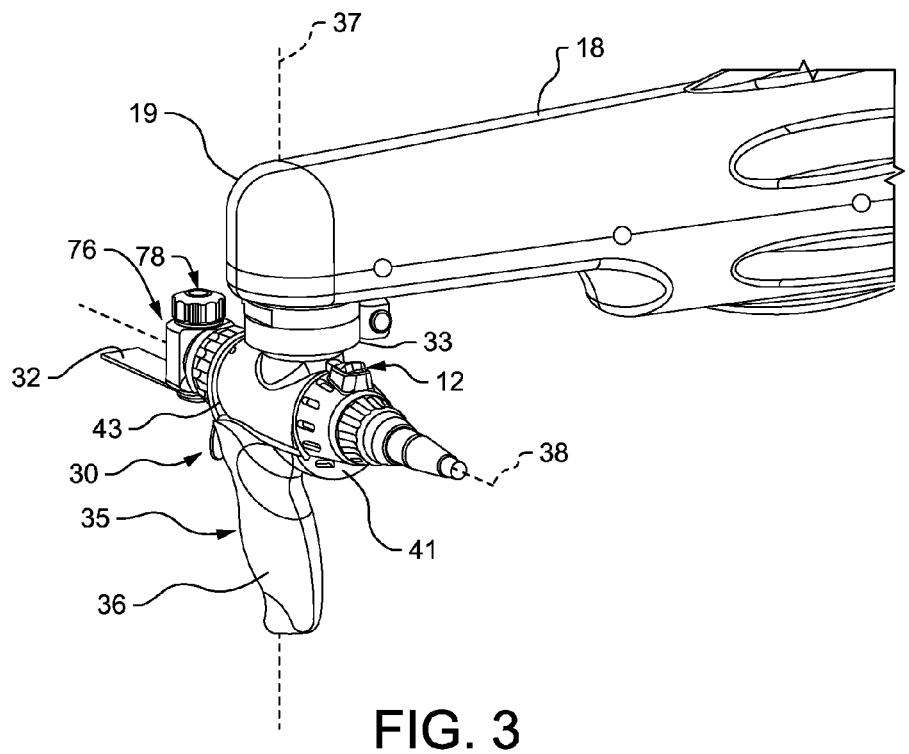
FIG. 3 is a partial perspective view of a robotic arm coupled to a disclosed surgical tool that includes a housing coupled to a surgical cutting implement and an adjustable handle.

Turning to FIG. 3, a disclosed surgical tool 30 is shown coupled to a distal end 19 of the articulated arm 18 of the robotic arm 15. In the embodiments shown in FIG. 3, the tool 30 includes a planar cutting device such as a saw 32. The plane of the saw 32 is ideally disposed in a fixed spatial relationship (or pose) with respect to the final joint or coupling 33 between the tool 30 and the distal end 19 of the arm 18. The fixed spatial relationship may also be between the saw 32 and the joint 34 of the robotic arm 15 (see FIGS. 1 and 2). Still referring to FIG. 3, the requirement that there be a fixed spatial relationship between the saw 32 and the coupling 33 (or the joint 34) can present an ergonomic problem for the surgeon. Specifically, the tool 30 includes a handle 35 that includes a grip 36. The position of the grip 36 as shown in FIG. 3 may not be desirable ergonomically for the surgeon. Thus, it may be more desirable for the surgeon to have the grip 36 in the tilted or angled position shown in FIG. 4 as opposed to the vertical position shown in FIG. 3.

However, because of the requirement of a fixed spatial relationship between the saw 32 and an element of the robotic arm 15 such as the coupling 33 or the joint 34, adjusting the position of the grip 36 has previously been impossible without moving the saw 32 thereby requiring the surgeon to reestablish the correct spatial relationship between the saw 32 and the coupling 33 or the joint 34 (or another aspect of the navigation system 11). To provide the surgeon with the ability to adjust the position of the handle 35 or grip 36 with out disrupting or effecting the position of the surgical implement (or saw 32 in this example), the surgical tool 30 is disclosed which enables the handle 35 to be rotated from the position shown in FIG. 3 to the position shown in FIG. 4 (and other positions as well) without effecting the pose of the surgical implement or saw 32. The design of the surgical tool 30 is illustrated in FIGS. 3-14.

Figure 4:
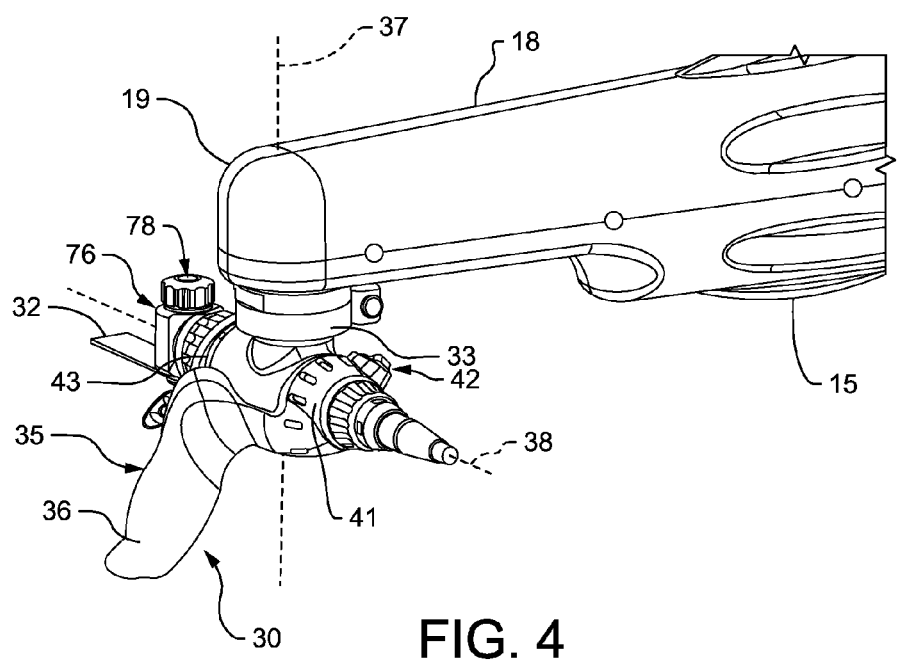
FIG. 4 is another partial perspective view of the robotic arm and surgical tool of FIG. 3 with the handle being rotated while the pose of the surgical cutting implement remains fixed relative to the robotic arm.

Still referring to FIGS. 3-4, the tool 30 is coupled to the distal end 19 of the arm 18 at the coupling 33. The coupling 33 allows the tool 30 to be rotated about the first axis 37 and between the various joints of the robotic arm 15, including the joint 34 (FIGS. 1-2) and the coupling 33, a desired pose for the saw 32 can be achieved. However, as illustrated in FIGS. 3-4, the pose of the saw 32 may require the handle 35 or grip 36 to be disposed in a poor ergonomic position. Assuming the vertical orientation illustrated in FIG. 3 is a poor ergonomic position for the grip 36, the surgeon is able to rotate the handle 35 to various positions, including the position shown in FIG. 4, which results in the handle 35 rotating about the second axis 38. The reader will note that the pose of the saw 32 remains unchanged in FIGS. 3-4, despite the rotation of the handle 35.

Figure 5:
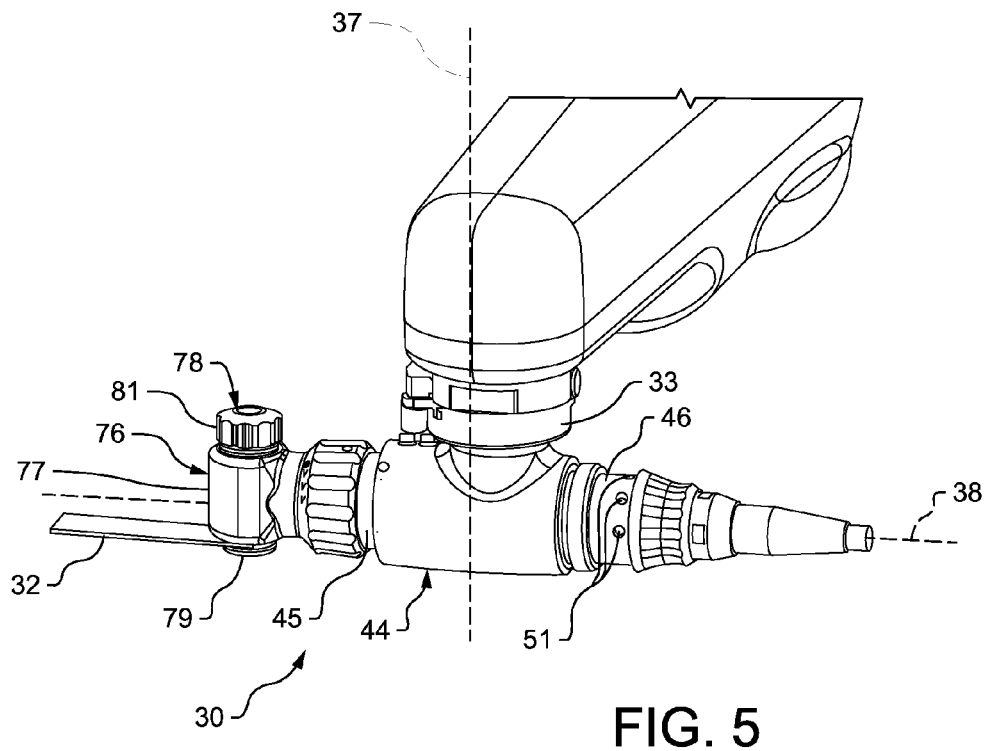
FIG. 5 is another partial perspective view of the robotic arm and surgical tool of FIGS. 3-4 with the rotating handle removed thereby exposing the housing, magnet ring and recesses in the housing used to adjust the position of the handle.
Figure 6:
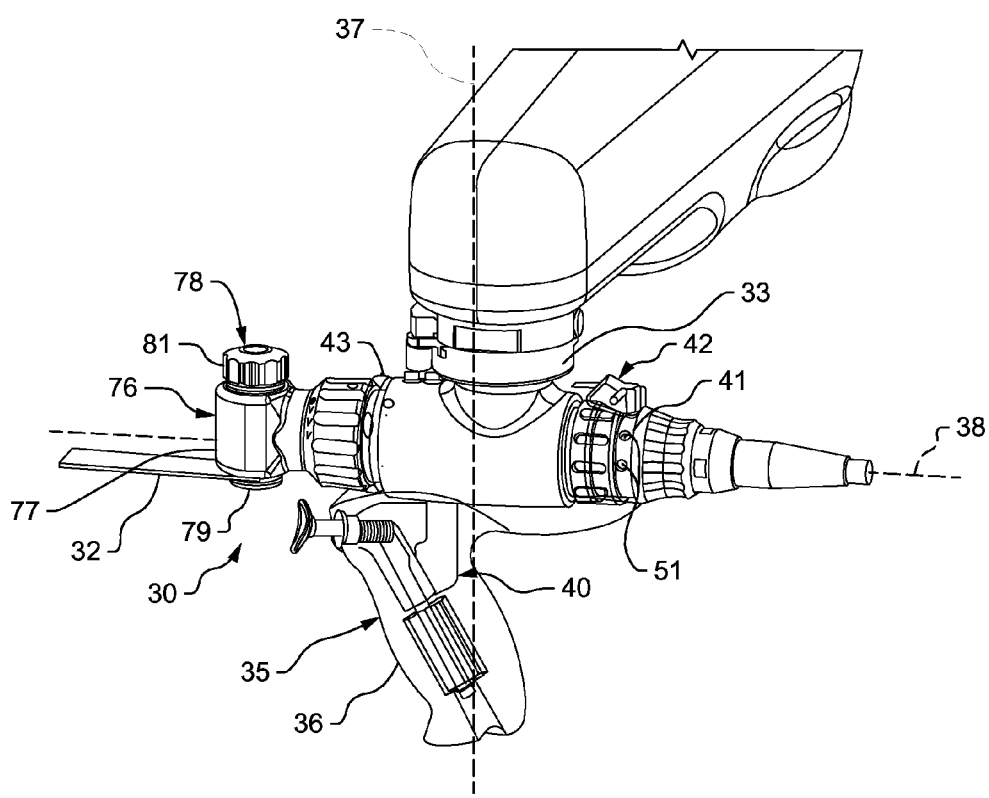
FIG. 6 is another partial perspective view of the robotic arm and surgical tool illustrated in FIGS. 3-5 with the handle portion being shown in phantom thereby illustrating the engagement of the lock assembly with one of the recesses in the housing and the trigger mechanism disposed in the handle.
Figure 7:
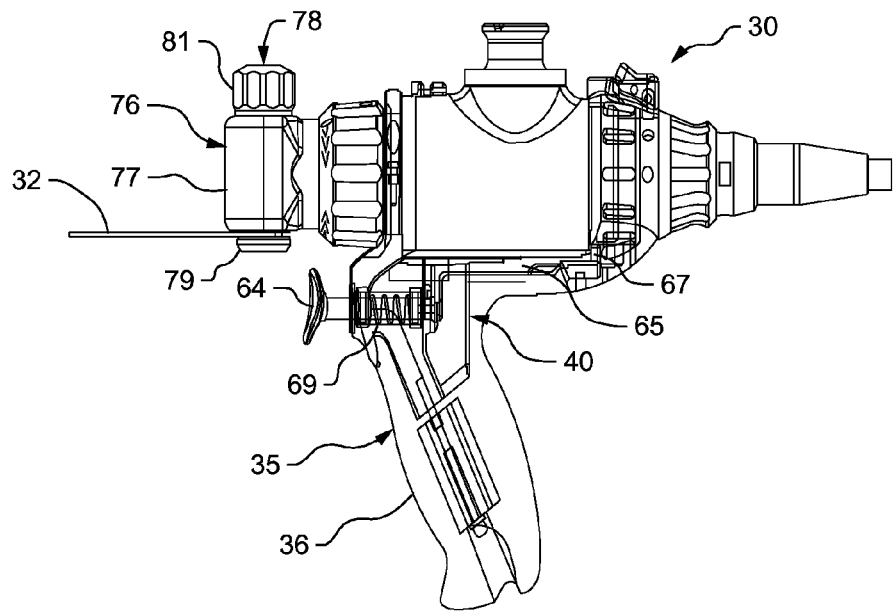
FIG. 7 is a side plan view of the surgical tool illustrated in FIGS. 3-6 with the handle shown in phantom and the robotic arm removed thereby illustrating the coupling element of the housing used to couple the housing to the final rotational degree of freedom of the robotic arm.
Figure 8:
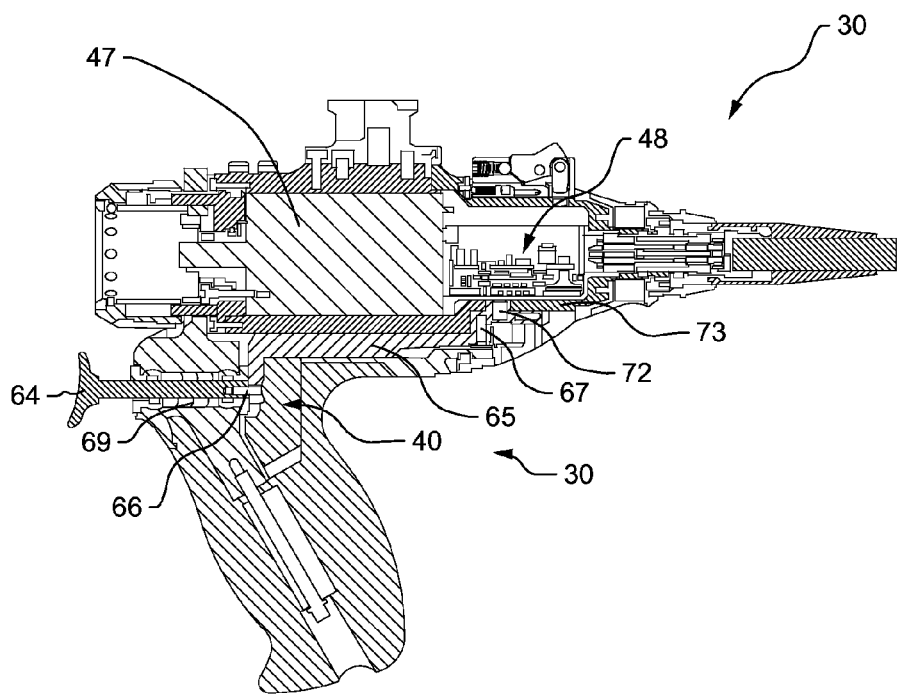
FIG. 8 is a sectional view of the surgical tool illustrated in FIGS. 3-7, illustrating the location of the motor and motor control electronics as well as the trigger mechanism.

This is accomplished using a unique handle/housing design as illustrated in FIGS. 5-6. Specifically, the handle 35 includes a grip portion 36 that serves as housing for a trigger mechanism shown generally at 40 in FIG. 6 and which will be described in greater detail in connection with FIGS. 7-8. The grip 36 is rigidly coupled to a sleeve 41 which includes a lock mechanism 42, which will be explained in greater detail in connection with FIGS. 9-12. In the embodiment illustrated, the grip 36 is also rigidly coupled to a loop 43. The loop 43 is disposed opposite the coupling 33 from the sleeve 41. The loop 43 and the sleeve 41 both accommodate portions of the housing 44 which, as shown in FIG. 5, includes a first end 45 and a second end 46. The housing 44 encloses a motor 47 and the electronics 48 of the surgical tool 30 as shown in FIG. 8. Returning to FIG. 5, the housing 44 also includes a plurality of recesses shown at 51 in FIGS. 5-6. The recesses 51 cooperate with the lock mechanism 42 to lock the handle 35 in a particular position defined by the engagement between the lock mechanism 42 and the chosen recess 51. In an embodiment, the recesses 51 extend around about half of the generally cylindrical housing 44 or provide an angular range of about 180°. However, rotations of greater than or less than 180 degrees are forcible and considered within the scope of the present disclosure.

Thus, the loop 43 rotatably accommodates the first end 45 of the housing 44 and the sleeve 41 rotatably accommodates the second end 46 of the housing 44. With the lock mechanism 42 released, the handle 35, loop 43 and sleeve 41 are free to rotate about the second axis 38. When the lock mechanism 42 has engaged at particular recess or is in a closed position as shown in FIG. 7, the sleeve is prevented from rotating about the second axis 38 and because the sleeve is connected to the handle 35 and loop 43, the sleeve 41, the handle 35 and the loop 43 cannot rotate about the second axis 38 when the lock mechanism 42 has been received in one of the recesses 51 as shown in FIGS. 6-7.

Figure 9:
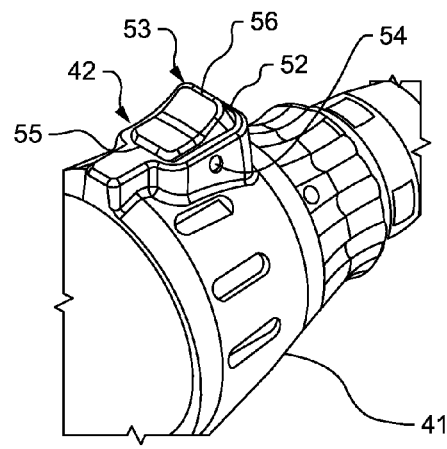
FIG. 9 is a partial perspective view of the surgical tool illustrated in FIGS. 3-8, particularly illustrating the button of the lock assembly that is mounted on the rotating sleeve portion of the grip handle assembly which rotates around the motor housing (44).

The lock mechanism 42 will now be described in greater detail in connection with FIGS. 9-12. The lock mechanism 42, as shown in FIG. 9, includes an outer shell 52 which accommodates a button 53. The button 53 is pivotally connected to the shell 52 and therefore the sleeve 41 by the pivot 54. The button 53 includes a first end 55 and a second end 56. The first end 55 of the button 53 is biased from the depressed or open position shown in FIG. 10 towards the closed or locked position shown in FIG. 11 by the combination of a biasing element such as a spring 57 and ball 58. The ball 58 fits into the indentation 59 disposed in the first end 55 of the button 53 when the first end 55 of the button 53 has been pressed downward to the open position shown in FIG. 10. Thus, in the embodiment illustrated in FIGS. 10-11, the indentation 59 and ball 58 may be employed to hold the button 53 in the upward, open or unlocked position shown in FIG. 10 while the sleeve 41, handle 35 and loop 43 are rotated about the second axis 38 to the desired recess 51. Because the indentation 59 is not deep, only a slight downward pressure on the second end 56 of the button 53 is necessary to move the lock mechanism 42 from the open position shown in FIG. 10 to the closed or locked position shown in FIG. 11.

Figures 10, 11:
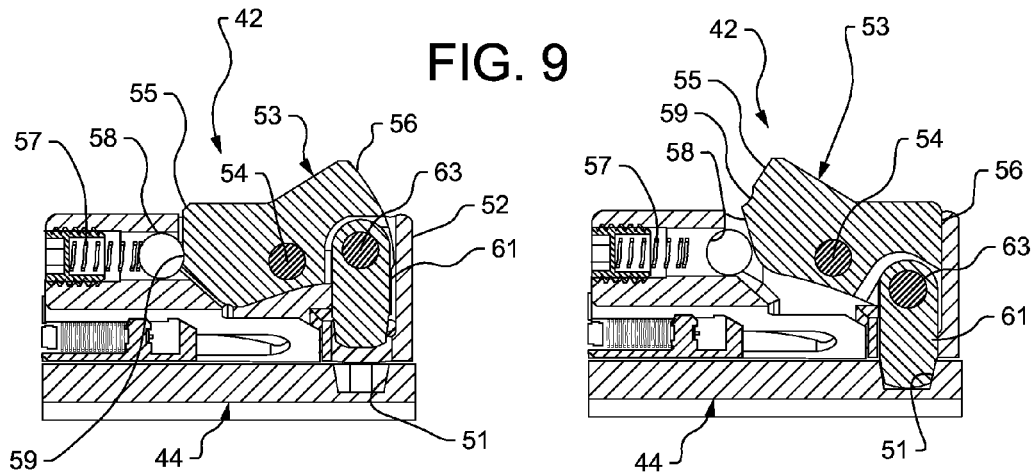
FIG. 10 is a cross sectional view of the lock assembly in an open position thereby enabling the handle to be rotated.
FIG. 11 is another cross sectional view of the lock assembly in a closed position, thereby preventing rotation of the handle.
Figure 12:
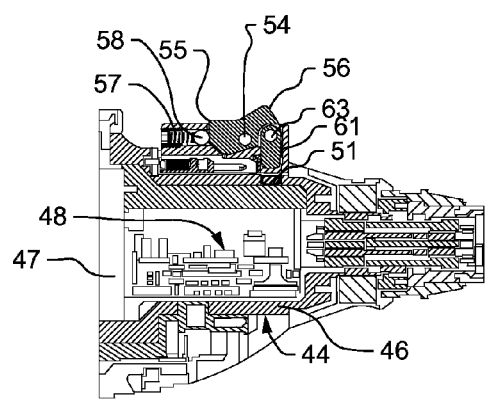
FIG. 12 is a partial cross sectional view of the surgical tool illustrated in FIGS. 3-11, illustrating the spatial relationships between the lock assembly, the tool electronics, the magnet and the link pin of the trigger mechanism.
Figure 13:
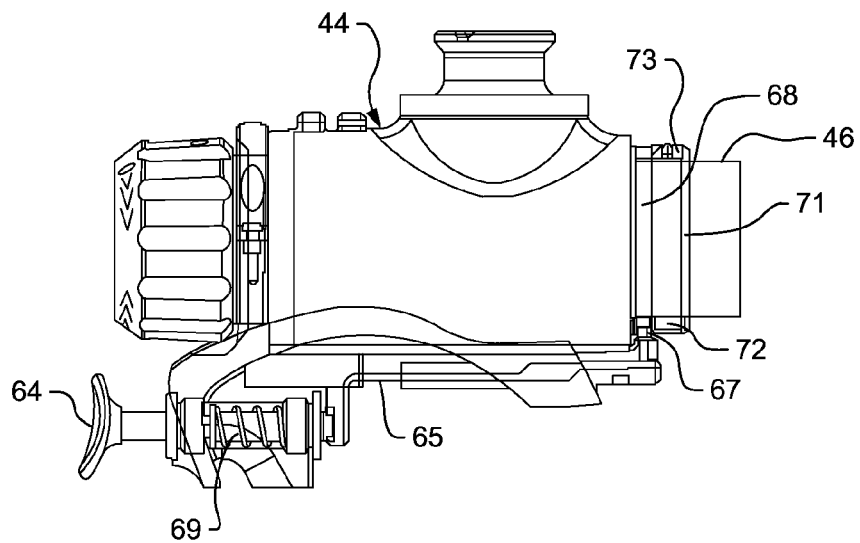
FIG. 13 is a partial side plan view of the surgical tool illustrated in FIGS. 3-12, particularly illustrating the trigger, link, link pin and magnet ring.

Also shown in FIGS. 10-12 is a lock rod 61 that is slidably coupled to the button 53 by the pin 63. The lock rod 61 may also be an integral part of the button 53. Upon release of the ball 58 from the indentation 59, the biasing action of the spring 57 and ball 58 on the first end 55 of the button 53 causes the button 53 to pivot in the clockwise direction from the orientation of FIGS. 10-11 thereby pressing the lock rod 61 downward and into the recess 51 as illustrated in FIG. 11. Downward pressure on the first end 55 of the button 53 causes the second end 56 of the button 53 to rotate in a counterclockwise direction with respect to the orientation of FIGS. 10-11 thereby raising the lock rod 61 out of the recess 51 as illustrated in FIGS. 10 and 12.

Therefore, to rotate the handle 35 from the position shown in FIG. 3 to an alternate position, such as that shown in FIG. 4, the user depresses the first end 55 of the button 53 which thereby raises or releases the lock rod 61 from one of the recesses 51. The sleeve 41, handle 35 and loop 43 are now free to rotate about the second axis 38 and the surgeon can rotate the handle 35 until the lock mechanism 42 is aligned with a desired recess 51 or recess 51 which puts the handle 35 in a more ergonomic position for the surgeon. Once the handle 35 is rotated to the desired position and the lock mechanism 42 is disposed over a desired recess 51, the second end 56 of the button 53 may be depressed slightly, thereby releasing the ball 58 from the indentation 59 and utilizing the bias of the spring 57 to pivot the button 53 and lock rod 61 downward into the desired recess thereby placing the handle 35 in the desired ergonomic position for the surgeon.

Figure 14:
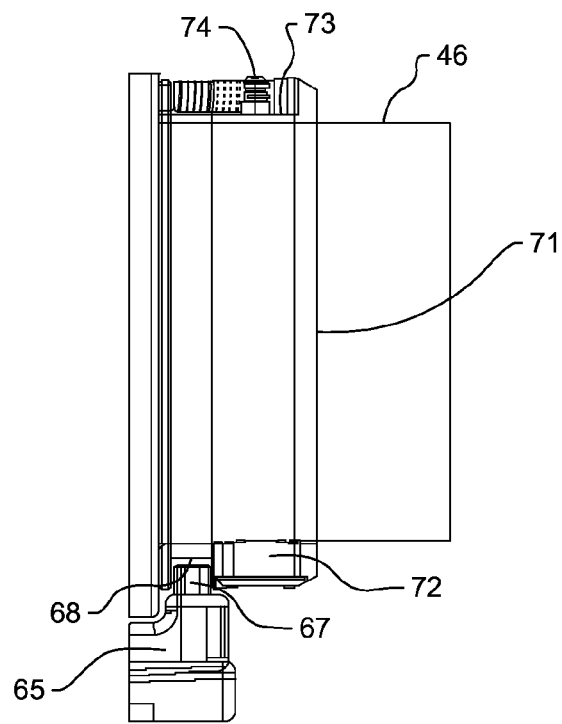
FIG. 14 is another partial side plan view of the surgical tool illustrated in FIGS. 3-13, particularly illustrating the distal end of the link and the link pin and how the link pin is disposed in a groove formed in the magnet ring.

Turning to FIGS. 7-8 and 13-14 the handle 35 also houses a trigger mechanism 40. The trigger mechanism 40 includes a trigger 64 which is biased towards the position shown in FIGS. 6-8 and 13 by a biasing element or the spring 69. The trigger 64 is coupled to a link rod 65 (see FIGS. 8 and 13) by the pin 66 or other suitable fastener (FIG. 8). The link rod 65 is coupled to a link pin 67. As shown in FIG. 14, the link pin 67 rides in the slot 68 disposed at the second end 46 of the housing 44 and defined by the second end 46 of the housing 44 and the magnet ring 71. The magnet ring 71 is coupled to a magnet 72 as best seen in FIG. 14. The magnet 72 is pushed or pulled along the second end 46 of the housing 44 by pressing or releasing the spring-biased trigger 64. The magnet ring 71 and magnet 72 are allowed to slide along the second end 46 of the housing 44 by way of a slot 73 (FIG. 8) disposed along an underside of the second end 46 of the housing 44. The magnet 72 rides in the slot 73 to prevent the magnet ring 71 from rotating as the magnet 72 needs to be positioned as close as possible to the Hall effect sensor mounted on the motor electronics 48. By having the magnet ride in this slot 73 cut into end 46 of the housing 44, the magnet 72 remains aligned with the Hall Effect sensors of the electronics 48 and the magnet 72 is positioned as close to the sensors as possible. The slot 73 and stud 74 prevent the ring 71 from rotating about the second axis 38 or the second end 46 of the housing 44.

The purpose of the magnet 72 is to adjust the speed of the motor. Specifically, the relative position of the magnet 72 with respect to the Hall effect sensors that form apart of the electronics 48 controls the speed of the motor 47. Thus, in addition to providing a handle 35 that can be rotated without effecting the position of the surgical implement 32, the handle 35 also provides a speed controlling trigger mechanism 40. Thus, despite its adjustability, the handle 35 also provides the critical function of speed control in addition to merely providing a grip 36 for the surgeon. While the speed control system disclosed herein includes the use of a magnet 72 and Hall effect sensors that are apart of the electronics 48, other speed control systems are available and will apparent to those skilled in the art. Further, while the surgical tool 30 is shown coupled to a saw 32 in the figures, the surgical tool 30 may be coupled to other surgical implements, such as a reamer, burr or other types of cutting devices. As shown in FIGS. 3-7, the surgical tool 30 is equipped with a clamp 76 that includes a ferrule 77 through which a threaded shaft 78 passes. The threaded shaft includes a flanged end 79 and a knob 81 which facilitates the clamping of the saw 32 between the flanged end 79 and the ferrule 77.

INDUSTRIAL APPLICABILITY

Thus, a surgical tool 30 is provided that may accommodate a variety of surgical implements including, but not limited to cutting elements such as reamers, burrs and saws and that can be coupled to the distal end 19 of an articulated arm 18 that forms part of an overall surgical robotic arm 15. The surgical tool 30 is coupled to the end 19 of the arm 18 by the coupling 33. During surgery, the pose of the surgical implement 32 is ideally an affixed spatial relationship with some aspect of the surgical robotic arm 15. For example, the saw 32 could be an affixed spatial relationship with a sensor disposed within the distal end 19 of the articulated arm 18 or a sensor disposed in the joint 34 (FIG. 2) of the surgical robotic arm 15. Arriving at the correct spatial relationship is important to have an accurate bone cut. Because the pose of the surgical implement 32 is crucial, the ergonomics of surgical tools can be compromised. For example, referring back to FIGS. 3-4, the handle 35 may be disposed in an uncomfortable position for the surgeon even though the saw 32 is in the correct pose.

The disclosed surgical tool overcomes this problem by providing a handle 35 that is rotatable with respect to the central housing 44 of the tool 30. By connecting the handle 35 to a sleeve 41 and a loop 43, the handle 35 can be rotatably coupled to the housing 44 thereby enabling the handle 35 to be rotated while the surgical implement 32 remains fixed in its pose. Thus, while the handle 35 rotates about the second axis 38, the surgical implement 32 remains stationary. The use of indentations 51 circumferentially spaced around the second end 46 of the housing 44 in combination with a lock mechanism 42 built into the sleeve 41 provides the surgeon with a variety of discrete positions in which the handle 35 may be locked. Obviously, a complete 360° rotation of the handle 35 is not necessary. Typically, the angle through which the handle 35 can rotate should be about 180° or less.

What is claimed is:

1. A surgical tool rotatably mounted to a robotic arm, the tool being rotatable about a first axis that is at least substantially vertical when the arm is in a horizontal position, the tool comprising:
   a housing coupled to the arm and rotatable about the first axis, the housing being at least substantially cylindrical and defining a second axis that is at least substantially perpendicular to the first axis;
   a handle including a grip coupled to a sleeve, the sleeve rotatably accommodating at least part of the housing;
   wherein, the handle may be rotated about the second axis while the housing remains fixed with respect to the second axis.

2. The surgical tool of claim 1, wherein the housing includes a plurality of recesses circumferentially spaced apart around the housing and about the second axis,
   the sleeve at least partially covering the recesses, the sleeve coupled to a lock assembly including a lock rod sized to be at least partially received one of the recesses at a time.

3. The surgical tool of claim 2 wherein the lock assembly further includes a button that engages the lock rod, the button and lock rod being biased so the lock rod is biased radially inwardly towards the recesses,
   wherein, when the button is pressed overcoming the radially inwardly bias and the lock rod is lifted radially outward beyond the recesses, the handle may be rotated about the second axis.

4. The surgical tool of claim 2 wherein the button includes a first end and a second end with a pivot pin disposed therebetween and coupled to the sleeve, the first end being biased outwardly by a spring causing the second end of the button to be biased inwardly towards the lock rod to move the lock rod towards the recesses.

5. The surgical tool of claim 2 wherein the lock rod is slidably coupled to the sleeve by a pin.

6. The surgical tool of claim 2 wherein the housing includes from 2 to about 10 recesses.

7. The surgical tool of claim 1 wherein the handle is rotatable about 180° around the housing and the second axis.

8. The surgical tool of claim 2 wherein the housing includes a first end coupled to a surgical implement, a second end that includes the recesses and the arm is coupled to the housing between the first and second ends.

9. The surgical tool of claim 1 wherein the housing is coupled to a surgical implement selected from the group consisting of a blade, a reamer and a burr.

10. The surgical tool of claim 1 wherein the handle is includes a loop that accommodates a first end of the housing and the sleeve accommodates a second end of the housing with the arm being coupled to the housing between the loop and the sleeve.

11. The surgical tool of claim 1 wherein the handle further includes a trigger, the trigger is coupled to a link, the link is coupled to a magnet,
   the housing enclosing a printed circuit board (PCB) including a Hall effect sensor, the PCB being disposed between the arm and the recesses,
   upon movement of by the trigger, the magnet being slidable across the Hall effect sensor with the housing disposed therebetween.

12. The surgical tool of claim 11 wherein the housing includes a first end and a second end with the arm being coupled to the housing between the first and second ends, the first end being coupled to a surgical implement,
   the magnet being coupled to a ring, the second end of the housing accommodating the ring and the sleeve with the ring disposed between the sleeve and the housing, the second end of the housing also enclosing the PCB,
   upon movement of the trigger, the magnet and ring being slidable across the Hall effect sensor with the housing disposed therebetween.

13. The surgical tool of claim 2 wherein the recesses are aligned in a plane that is at least substantially perpendicular to the second axis.

14. A surgical robotic system, comprising:
   a robotic arm;
   a tool rotatably mounted to the robotic arm, the tool being rotatable about a first axis that is at least substantially vertical when the arm is in a horizontal position, the tool including a housing coupled to the arm;
   the housing being at least substantially cylindrical and defining a second axis that is at least substantially perpendicular to the first axis, the housing being coupled to a surgical implement, the housing including a plurality of recesses circumferentially spaced apart around the housing and about the second axis and aligned in plane at least substantially perpendicular to the second axis, the housing being rotatable with the tool about the first axis but not about the second axis;
   a handle including a grip coupled to a sleeve, the sleeve rotatably accommodating at least part of the housing and at least partially covering the recesses, the sleeve coupled to a lock assembly including button including a lock rod sized to be at least partially received in one of the recesses at a time, the button and lock rod being biased so the lock rod is biased radially inwardly towards the recesses;
   wherein, when the button is pressed overcoming the radially inwardly bias and the lock rod is lifted radially outward beyond the recesses, the handle may be rotated about the second axis while the housing and surgical implement remain fixed with respect to the second axis.

15. The surgical robotic system of claim 14 wherein the button includes a first end and a second end with a pivot pin disposed therebetween and coupled to the sleeve, the first end being biased outwardly by a spring causing the second end to be biased inwardly towards the lock rod to move the lock rod towards the recesses.

16. The surgical robotic system of claim 14 wherein the lock rod is slidably coupled to the sleeve by a pin.

17. The surgical robotic system of claim 14 wherein the housing includes from 2 to about 10 recesses.

18. The surgical robotic system of claim 14 wherein the handle is rotatable about 180° around the housing and the second axis.

19. The surgical robotic system of claim 14 wherein the housing includes a first end coupled to a surgical implement, a second end that includes the recesses and the arm is coupled to the housing between the first and second ends.

20. The surgical robotic system of claim 14 wherein the surgical implement is selected from the group consisting of a blade, a reamer and a burr.

21. The surgical robotic system of claim 14 wherein the handle is also coupled to a loop and the housing includes a first end and a second end, the sleeve accommodating the second end of the housing and the loop accommodating the first end of the housing.

22. The surgical robotic system of claim 14 wherein the handle further includes a trigger, the trigger is coupled to a link, the link is coupled to a magnet,
   the housing enclosing a printed circuit board (PCB) including a plurality of Hall effect sensors, the PCB being disposed between the arm and the recesses,
   upon movement of the trigger, the magnet being slidable along the Hall effect sensors with the housing disposed therebetween.

23. The surgical robotic system of claim 22 wherein the housing includes a first end and a second end with the arm being coupled to the housing between the first and second ends, the first end being coupled to a surgical implement,
   the magnet being coupled to a ring, the second end of the housing being accommodated in the ring and the sleeve with the ring disposed between the sleeve and the housing, the second end of the housing also enclosing the PCB,
   upon movement of the trigger, the magnet and ring being slidable along the Hall effect sensors with the housing disposed therebetween.

24. A method for rotating a grip of a surgical tool while maintaining a surgical implement of the surgical tool in a fixed position, the method comprising:
   rotatably mounting the surgical tool to a robotic arm, the tool being rotatable about a first axis that is at least substantially vertical when the arm is in a horizontal position, the tool including a housing coupled to the arm and rotatable about the first axis, the housing being at least substantially cylindrical and defining a second axis that is at least substantially perpendicular to the first axis, the surgical tool further including a handle including a grip coupled to a sleeve, the sleeve rotatably accommodating at least part of the housing, the sleeve coupled to a lock assembly;
   releasing the lock assembly from a first locked position;
   rotating the handle to a second position about the second axis while the housing remains fixed with respect to the second axis; and
   moving the lock assembly to a second locked position.

25. The method of claim 24 wherein the releasing of the the lock assembly from the first locked position is performed against the bias of a spring.

26. The method of claim 24 wherein the housing includes at least two recesses aligned with the lock assembly that receive part of the lock assembly in the first and second locked positions.

27. The method of claim 26 wherein the housing includes from 2 to about 10 recesses.

28. The method of claim 27 wherein a maximum angle between any two recesses with respect to the second axis is about 180°.

29. The method of claim 24 wherein the housing is coupled to a surgical implement selected from the group consisting of a blade, a reamer and a burr.

30. The method of claim 24 wherein the handle further includes a trigger, the trigger is coupled to a link, the link is coupled to a magnet, the housing encloses a printed circuit board (PCB) including a Hall effect sensor the housing also encloses a motor coupled to a surgical implement, the method further including
   adjusting a speed of the motor by moving the magnet with the link and sliding the magnet across the Hall effect sensor with the housing disposed there between.

* * * * *